United States Patent
Winkler et al.

(10) Patent No.: US 11,091,408 B2
(45) Date of Patent: Aug. 17, 2021

(54) INTEGRATION OF CARBON DIOXIDE ABSORPTION AND WATER ELECTROLYSIS INTO METHANATION

(71) Applicants: Shahar Technology Solutions Ltd., Jerusalem (IL); Ariel Scientific Innovations Ltd., Ariel (IL)

(72) Inventors: Nathan H. Winkler, New York, NY (US); Michael V. Sassoon, Karkur (IL); Gady Golan, Rishon Lezion (IL); Shlomo A. Zerbib, Elon Moreh (IL)

(73) Assignees: Shahar Technology Solutions Ltd.; Ariel Scientific Innovations Ltd.

( * ) Notice: Subject to any disclaimer, the term of this patent is extended or adjusted under 35 U.S.C. 154(b) by 0 days.

(21) Appl. No.: 16/817,766

(22) Filed: Mar. 13, 2020

(65) Prior Publication Data

US 2020/0392053 A1    Dec. 17, 2020

Related U.S. Application Data

(60) Provisional application No. 62/860,329, filed on Jun. 12, 2019.

(51) Int. Cl.
*C07C 1/04* (2006.01)
*B01D 53/26* (2006.01)
(Continued)

(52) U.S. Cl.
CPC ........ *C07C 1/0485* (2013.01); *B01D 53/0438* (2013.01); *B01D 53/1425* (2013.01); *B01D 53/1475* (2013.01); *B01D 53/1493* (2013.01); *B01D 53/261* (2013.01); *B01D 53/263* (2013.01); *B01D 53/265* (2013.01); *C02F 1/04* (2013.01); *C25B 1/04* (2013.01); *B01D 2252/2056* (2013.01);
(Continued)

(58) Field of Classification Search
CPC .......... B01D 53/73; B01D 53/62; C10G 2/50; C25B 1/04; C10L 3/08
See application file for complete search history.

(56) References Cited

U.S. PATENT DOCUMENTS

| | | | |
|---|---|---|---|
| 5,183,484 A * | 2/1993 | Yamaguchi | ........ B01D 53/047 95/99 |
| 2005/0132884 A1 | 6/2005 | Xu et al. | |

(Continued)

FOREIGN PATENT DOCUMENTS

| | | |
|---|---|---|
| DE | 102012007136 | 10/2013 |
| DE | 102013110470 | 3/2015 |

(Continued)

OTHER PUBLICATIONS

WO 2016115582A , Jul. 28, 2016, machine translation.*
(Continued)

*Primary Examiner* — Jafar F Parsa
(74) *Attorney, Agent, or Firm* — Lieberman & Brandsdorfer, LLC

(57) ABSTRACT

A method and system are provided to recover water and carbon dioxide from combustion emissions. The recovery includes, among other things, electrolysis and carbon dioxide capture in a suitable solvent. The recovered water and carbon dioxide are subject to reaction, such as a catalytic methanation reaction, to generate at least methane.

29 Claims, 3 Drawing Sheets

(51) Int. Cl.
  *B01D 53/04*  (2006.01)
  *B01D 53/14*  (2006.01)
  *C02F 1/04*  (2006.01)
  *C25B 1/04*  (2021.01)
  *C02F 103/18*  (2006.01)
(52) U.S. Cl.
  CPC .... *B01D 2257/504* (2013.01); *B01D 2257/80* (2013.01); *B01D 2259/40088* (2013.01); *C02F 2103/18* (2013.01)

(56) References Cited

U.S. PATENT DOCUMENTS

| | | | |
|---|---|---|---|
| 2009/0238742 A1 | 9/2009 | Liu et al. | |
| 2012/0222426 A1 | 9/2012 | Macadam | |
| 2013/0177481 A1* | 7/2013 | Hokari | B01D 53/1475 422/106 |
| 2013/0272939 A1 | 10/2013 | Liu et al. | |
| 2017/0274317 A1 | 9/2017 | Bumb | |

FOREIGN PATENT DOCUMENTS

| | | | |
|---|---|---|---|
| DE | 102013002021 | 6/2015 | |
| EP | 1936128 | 6/2008 | |
| EP | 2751307 | 7/2014 | |
| JP | 2004261757 | 9/2004 | |
| WO | WO2013/029701 A1 | 3/2013 | |
| WO | WO-2013124632 A2 * | 8/2013 | C25B 9/18 |
| WO | 2013190581 | 12/2013 | |

OTHER PUBLICATIONS

Van der Zwet et al., improved gas treating with sulfinol-x, Abstract only (Sulfur (2010), 326, 53-57).*
David W. Keith et al., A Process for Capturing CO2 from the Atmosphere, Joule 2, 1573-1594 (Aug. 15, 2018).
A.P.H. Goede, CO2-Neutral Fuels, EPJ Web of Conferences 98, 07002, Dutch Institute for Fundamental Energy Research (2015).
Hsin-Ta Hsueh et al., Removal of CO2 from Flue Gas with Ammonia Solution in a Packed Tower, J. Environ. Eng. Manage., 20(1), 1-7 (2010).
Bryce Dutcher et al., Amine-Based CO2 Capture Technology Development from Beginning of 2013—A Review, ACS Applied Materials & Interfaces, 7, 2137-2148 (2015).
G. Granitsiotis, Methanation of Carbon Dioxide, Experimental Research of Separatioan Enhanced Methanation of CO2 (2017).
Hassan Ghanbarabadi et al., Simulation of CO2 Removal from Ethanwith Sulfinol-M+AMP Solvent . . . , Petroleum 5, 90-101 (2019).
Oliver Seyboth et al., Development of a Spray Scrubbing Process for Post Combustion CO2 Capture with Amine Based Solvents, Energy Procedia 63, 1667-1677 (2014).
Bingtao Zhao et al., Mass transfer performance of CO2 capture in rotating packed bed: Dimensionless modeling and intelligent prediction, Applied Energy 136, 132-142 (2014).
International Search Report PCT/US2020/036063.
Written Opinion PCT/US2020/036063.
Zhiwu Liang et al., Review on current advances, future challenges . . . For post-combustion CO2 capture using amine-based absorbents, Chinese J. of Chem. Eng'g 24, 278-88 (2016).
Xiaomei Wu et al., Overall mass transfer coefficient of CO2 absorption in a diameter-varying spray tower, Energy Procedia 114, 1665-1670 (2017).
Hanna Karlsson et al., Rate of absorption of CO2 absorption systems using a wetted wall column, Energy Procedia 114, 2009-2023 (2017).
Hongyi Dang, et al., CO2 absorption rate and solubility in monoethanolamine/piperazine/water, Separation Science and Tech., vol. 38, No. 2, 337-357 (2003).
Mohammad Heydarifard et al., Reactive absorption of CO2 into piperazine . . . modeling and experimental, Int'l J. of Greenhouse Gas Control 79, 91-116 (2018).
Jia-Lin Kang et al., Comparison between packed beds and rotating packed beds for CO2 capture using monoethanolamine . . . , Int'l J. of Greenhouse Gas Control 46, 228-229 (2016).
M.R. Aliff Radzuan et al., Sustainable optimization of natural gas sweetening using a process simulation approach . . . , Materials Today: Proceedings 19, 1628-1637 (2019).
Chintana Saiwan et al., Part 3: Corrosion and preventoin in post-combustion CO2 capture systems, Carbon Management, 2:6, 659-675 (2014).

* cited by examiner

INTEGRATION OF CARBON DIOXIDE ABSORPTION AND WATER ELECTROLYSIS INTO METHANATION

CROSS REFERENCE TO RELATED APPLICATION(S)

This application claims the benefit of priority to U.S. Provisional Application No. 62/860,329 filed in the U.S. Patent & Trademark Office on Jun. 12, 2019, the disclosure of which is incorporated herein by reference.

BACKGROUND

Embodiments disclosed herein relate to methods and systems for the integration of carbon dioxide absorption and water electrolysis into a methanation reaction system.

Signatories to the Paris Climate Agreement are committed to steep reductions in greenhouse gas emissions, which include carbon dioxide, over the coming decade. The technological and economic challenge of meeting emission reductions under the Paris Climate Agreement is extremely significant. Fossil fuel-reliant industries such as power generation and manufacturing that output high levels of greenhouse gas emissions are especially vulnerable to new regulations that are rapidly reducing their profitability.

One solution for meeting the goals of the Paris Climate Agreement is renewable energy. Renewable energy is cheap and abundant when and where it is available. The problem is renewable energy sources are not always available or plentiful. Unlike fossil fuels, which are dispatchable on demand to produce electricity or heat for satisfying consumer and business energy needs, photovoltaic (PV) solar power is plentiful for typically less than 40% of the time, i.e., during peak sunlight hours. Wind turbines depend on environmental wind as a natural renewable energy resource; wind speeds can fluctuate greatly over the course of a day and are not abundant in many locales. Accordingly, the complete elimination of non-renewable energy sources is, at the present time, likely infeasible given the world energy demands.

Elimination of reliance on non-renewable energy depends on the development of methods for storing renewable energy over long periods of time, embodiments disclosed herein make use of combustion emission streams or exhaust, such as from, for example, a conventional electricity production plant, as a source of renewable energy by processing the exhaust and subjecting processing products to a methanation reaction system to produce methane for use in satisfying further energy demands.

SUMMARY

Embodiments disclosed herein relate to methods and systems for processing emissions from, e.g., a hydrocarbon combustion appliance, such as one that forms part of a conventional electricity production plant, to provide carbon dioxide and hydrogen, and subjecting the carbon dioxide and hydrogen to reaction for the production of combustible reagents such as methane, that can be, for example, compressed, stored, recycled to the hydrocarbon combustion appliance, and/or put to other uses.

In an embodiment, a method includes receiving a hydrocarbon combustion exhaust stream comprising water and carbon dioxide and removing at least a portion of water to at least partially dry the hydrocarbon combustion exhaust stream. The carbon dioxide is separated from the at least partially dried hydrocarbon combustion exhaust stream. The carbon dioxide separation includes at least capturing the carbon dioxide in a solvent, heating the solvent and the captured carbon dioxide, and removing the carbon dioxide from the heated solvent. The water removed from the hydrocarbon combustion exhaust stream is subjected to electrolysis to generate hydrogen. The generated hydrogen and the separated carbon dioxide are subjected to reaction to generate one or more hydrocarbons, including at least methane.

In another embodiment, a system includes a condensate tank configured to receive a hydrocarbon combustion exhaust stream including at least water and carbon dioxide and condense steam in the hydrocarbon combustion exhaust stream. A desiccant dehumidifier configured to at least partially dry the hydrocarbon combustion exhaust stream is provided. The system further includes at least one separation apparatus configured to separate the carbon dioxide from the at least partially dried hydrocarbon combustion exhaust stream. The at least one separation apparatus is configured to capture the carbon dioxide in a solvent, heat the solvent, and separate the carbon dioxide from the heated solvent. It should be understood that the separation apparatus, like other equipment described herein, may comprise one or more apparatus. An electrolysis apparatus is configured to receive water removed from the at least partially dried hydrocarbon combustion exhaust stream and to carry out electrolysis on the water to generate hydrogen. A reactor is configured for reaction between the generated hydrogen and the separated carbon dioxide to generate one or more hydrocarbons, including at least methane.

Other aspects of the invention, including apparatus, devices, systems, sub-systems, assemblies, sub-assemblies, processes, methods, and the like, which constitute part of the invention, will become more apparent upon reading the following detailed description of the exemplary embodiments.

BRIEF DESCRIPTION OF THE DRAWINGS

The accompanying drawings are incorporated in and constitute a part of the specification. Features shown in the drawings are meant as illustrative of only some embodiments, and not of all embodiments, unless otherwise explicitly indicated. In such drawings.

DETAILED DESCRIPTION OF THE EXEMPLARY EMBODIMENTS AND EXEMPLARY METHODS

It will be readily understood that the components of the present embodiments, as generally described and illustrated in the Figures incorporated herein, may be arranged and designed in a wide variety of different configurations. Thus, the following detailed description of the embodiments of the apparatus, system, and method of the present embodiments, as presented in the Figures, is not intended to limit the scope of the embodiments, as claimed, but is merely representative of selected embodiments.

Reference throughout this specification to "a select embodiment," "one embodiment," or "an embodiment" means that a particular feature, structure, or characteristic described in connection with the embodiment is included in at least an embodiment. Thus, appearances of the phrases "a select embodiment," "in one embodiment," or "in an embodiment" in various places throughout this specification are not necessarily referring to the same embodiment. The various embodiments may be combined with one another in various combinations that would be understood to those skilled in the art having reference to this disclosure.

The illustrated embodiments will be best understood by reference to the drawings, wherein like parts are designated by like numerals throughout. The following description is intended only by way of example, and simply illustrates certain selected embodiments of systems, processes, steps, apparatus, and equipment that are consistent with the embodiments.

Figure 1:
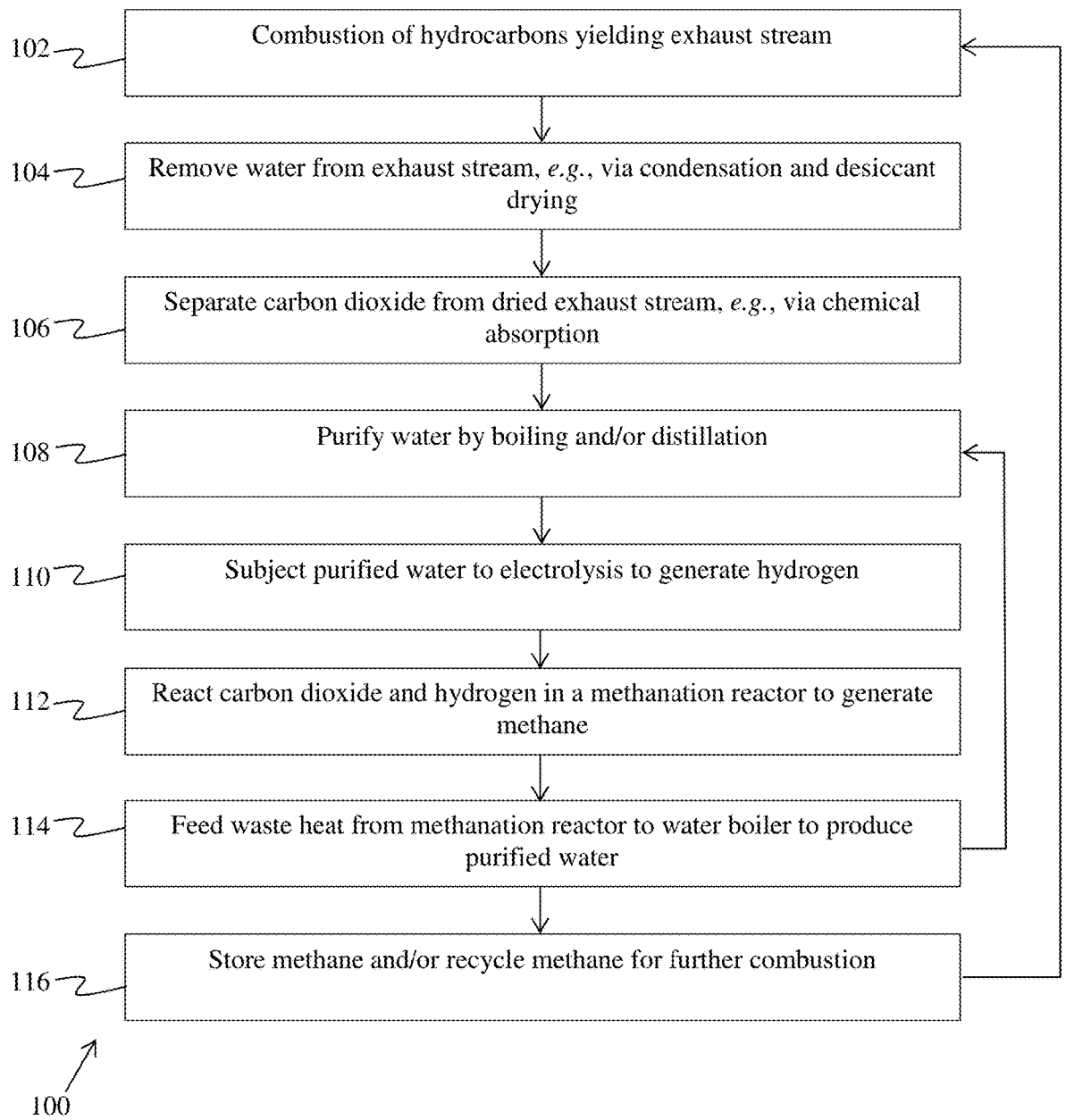
FIG. 1 is a simplified flow chart of an overall method according to an exemplary embodiment.
Figure 2:
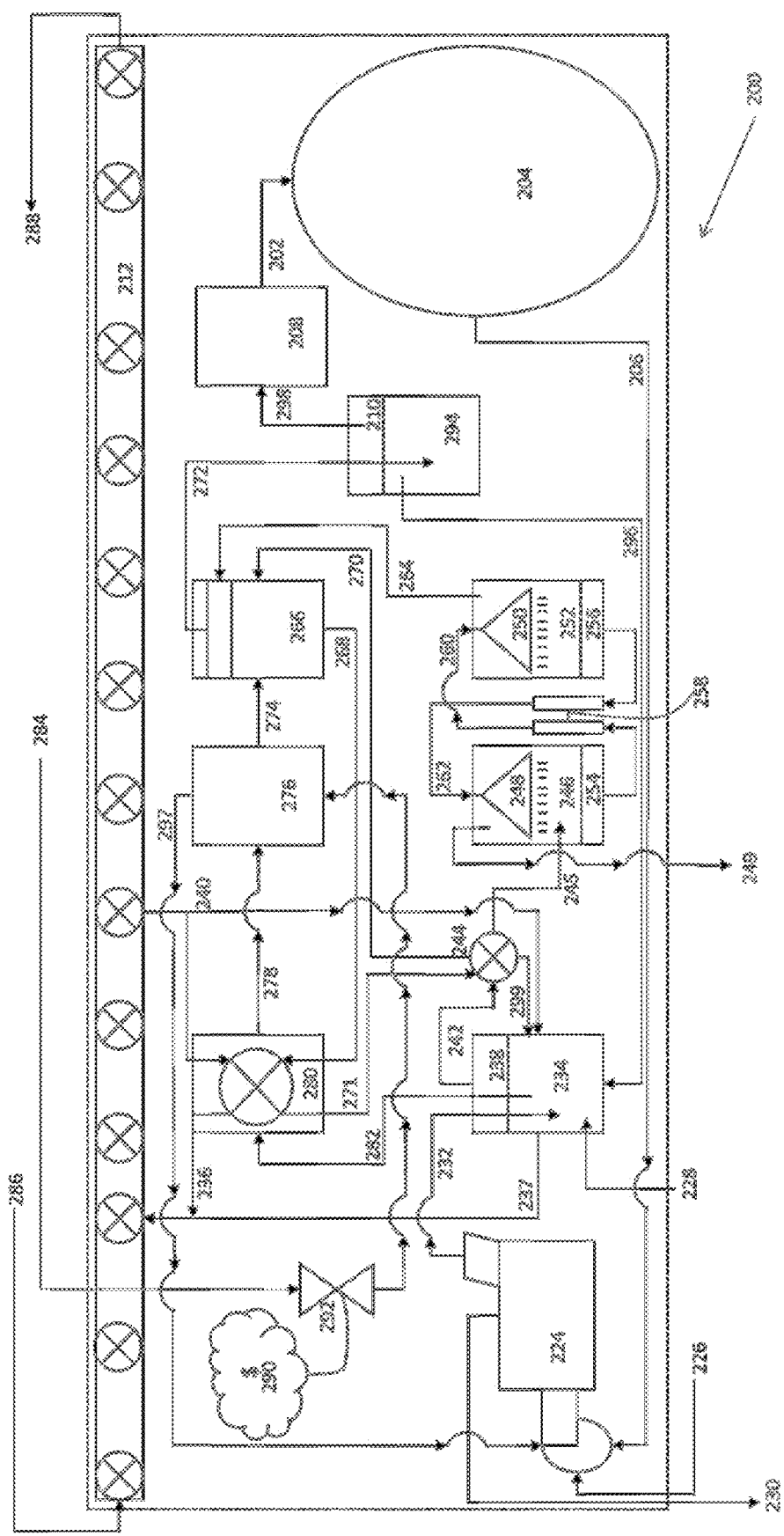
FIG. 2 is a schematic flow diagram of a system according to an exemplary embodiment that may be used for carrying out the method of FIG. 1.

Exemplary embodiments are now described with respect to a process (100) of FIG. 1 and a system (200) of FIG. 2.

In step (102) of FIG. 1, an exhaust stream/emissions is received, typically from one or more hydrocarbon combustion appliances and/or plants, such as an electricity generation plant. Combustion of hydrocarbons is the basis for most processes and systems that underpin modern economies. Combustion equipment includes, but is not limited to, boilers for producing hot water and steam, furnaces for producing hot air, internal combustion engines for vehicles in transportation, turbines for power generation and jet propulsion, rocket nozzles for missile and spacecraft thrust, industrial kilns, smelting processes for producing steel, etc. These apparatus exhaust mixtures of carbon dioxide, carbon monoxide, water, nitrogen, trace gases (e.g., nitrogen oxides, sulfur oxides, argon, etc.), or combinations thereof, typically as a result of combustion. Carbon dioxide and water typically compose more than 99% of the mass concentration of the non-nitrogen exhaust during the combustion of hydrocarbons and air. Carbon monoxide may be present in significantly smaller quantities depending on the excess air ratio used during combustion. The ratios may vary according to the combustion process and input material.

In the embodiment illustrated in FIG. 2, the system (200) includes a combustion reactor or other appliance (224) from which an exhaust gas (232) is emitted. The combustion appliance (224) typically burns a hydrocarbon such as methane in the presence of an oxygen source such as air (226), emitting the exhaust gas (232) containing carbon dioxide, nitrogen, and water, which may be present in various physical forms, such as steam, vapor, and liquid. Exemplary embodiments are designed to handle mixed exhaust streams that contain some or all of the constituents described above.

According to an embodiment, the exhaust gas (232) leaves the combustion appliance (224) in step (102) at a temperature of, for example, approximately 100° C. to 200° C. The exhaust gas typically contains gaseous water at a proportion of, for example, as much as 10% of the total mass of the exhaust.

In step (104), at least a portion of the water from the emissions output from step (102) is removed. In exemplary embodiments, water removal (104) involves, for example, condensation and/or desiccant drying. In an exemplary embodiment, the water-removal step (104) involves injection of the emissions into a water bath to condense part, and more preferably all, of the steam in the emissions. In an exemplary embodiment, injection of the emissions into the water physically contacts the emissions with and mixes the emissions with the water. In an exemplary embodiment, all, or substantially all, of the remaining water vapor is removed via exposure to a desiccant that absorbs all, or substantially all, or the remaining moisture. In an exemplary embodiment, the resulting gas mixture is substantially or fully dry or water free. In exemplary embodiments, the resulting gas mixture contains 0 to 3 weight percent water, 0 to 2 weight percent water, or 0 to 1 weight percent water, or less than 0.1 weight percent water. In an alternative embodiment, water removal may be omitted, in which case water may be present at about 10 weight percent, in which case the system will operate at a reduced efficiency, e.g., additional electricity may be required to separate the carbon dioxide from nitrogen in step (106) and the kinetic rate constant of the methanation reaction in step (112) may be reduced due to the presence of water inhibiting the reaction.

In step (104), the water is removed from the mixed exhaust stream in order to obtain relatively pure carbon dioxide for later processing in the methanation reactor. Removal of water from the emission stream is desirable because unprocessed water inhibits the methanation reaction given that water is one of reaction products of methanation, as shown in equation 1 below. Thus, unremoved water that makes its way to the reactor pushes the rate constant to the left and decreases the kinetic reaction rate.

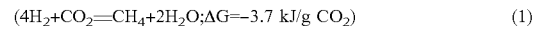

$$(4H_2+CO_2=CH_4+2H_2O; \Delta G=-3.7 \text{ kJ/g } CO_2) \quad (1)$$

The system (200) of FIG. 2 illustrates an embodiment of suitable equipment for carrying out the water-removal step (104), and in an embodiment, equipment for applying a two-step water removal process. First, the system (200) includes a condensate tank (234) containing a fixed or predetermined amount of water. The exhaust stream (232) is injected into the water in order to immediately condense the exhaust stream and lower its temperature to about 20° C., thereby condensing the steam. If needed or desired, an additional amount of water (or "make-up water") can be added to the condensate tank (234) via line (228), such as to keep the water level within the condensate tank (234) relatively constant.

Carbon dioxide and water vapor remaining in an upper chamber area (238) of the condensate tank (234), above the liquid water, is removed and fed (242) to a desiccant dryer (244) for drying. Desiccants include, but are not limited to, salts, zeolites, activated carbon, and other high surface area materials. In an embodiment, the desiccants are regenerated via the addition of heat, which may be harvested from a methanation reactor (266), discussed further below. In an exemplary embodiment, this heat is harvested via passing a heat transfer fluid (271) between the distillation reactor or unit (280) and a heat exchanger in the desiccant dryer (244) in order to continuously regenerate the desiccant. The heat transfer fluid (270) is then fed back to the methanation reactor (266) where it is re-heated and fed (268) first to the distillation unit (280) where it is cooled to between 100° C. and 150° C. and then fed (271) to the desiccant dryer (244) where it is further cooled to between 90° C. and 140° C. prior to being fed (270) back to the methanation reactor (266) for reheating. In an embodiment, the heat transfer is achieved with a rotating contact reactor or similar configuration where the desiccant is continuously rotating so that on one side the desiccant is heated and the evaporated water is collected and fed (299) back to the condensate tank (234) while the unheated side of the desiccant is exposed to the gas stream (242) and removes the remaining water. In an exemplary embodiment, the resulting at least partially dried emissions (245) leaving the desiccant dryer (244) comprises, consists essentially of, or consists of carbon dioxide, nitrogen, and trace gases.

In step (106), carbon dioxide is removed from the at least partially dry emissions via chemical absorption.

In an embodiment, in particular the system (200) of FIG. 2, the at least partially dry emissions (245) is a gas mixture containing carbon dioxide. The dry emissions (245) are introduced into a separation apparatus that, in an exemplary embodiment, comprises a first reactor or separation vessel (246), a second reactor or separation vessel (252), and a liquid-to-liquid heat pump or heat exchanger (258).

The first separation vessel (246) separates the carbon dioxide from the nitrogen and any other gases typically present in trace amounts. In the first separation vessel (246), the at least partially dry emissions (245) are injected under a nozzle (248) that sprays a fine mist of a carbon dioxide solvent (delivered via (262), discussed below). The carbon dioxide solvent is combined with the dry emissions (245) in order to capture (or absorb) the carbon dioxide, in an exemplary embodiment to saturation. Representative solvents for carbon dioxide capture include Selexol® (dimethyl ethers of polyethylene glycol (DEPG)), Fluor solvent (propylene carbonate), Purisol (N-methl-2-pyrrolidone), Rectisol (methanol), a sulfinol solvent (a mixture of diisopropanolamine or methyl diethanolamine (MDEA), sulfinol (containing sulfolane, tetrahydrothiophene dioxide and water), econamine FG (amine-based), and ionic liquids (e.g., 1-butyl-3-propylamineimidazolium tetrafluoroborate). In an exemplary embodiment, the solvent comprises a sulfinol solvent or an equivalent solvent. Temperature in the first separation vessel (246) may be conducive to capturing the carbon dioxide in the solvent. In the case of a sulfinol solvent, a temperature of, for example, 20° C. is useful. The resulting solvent with captured carbon dioxide falls via gravity to a bottom chamber (254) of the first separation vessel (246). In an embodiment, the relatively cool solvent (e.g., a sulfinol solvent) is saturated at this point. The nitrogen and any trace gases in the first separation vessel (246) are vented (249) from the top of the first separation vessel (246) into the atmosphere. Nitrogen is a non-polar diatomic molecule that typically does not chemically bind to the solvent, whereas the carbon dioxide does, thus explaining why the nitrogen is not captured by the solvent falling into the bottom chamber (254). The mechanism for the capture of carbon dioxide by the solvent is unique to each solvent. Without wishing to be bound by any theory, in the case of the above-mentioned embodiment with sulfinol, the mechanism is related to the bonding between the hydrogen atoms in the sulfinol to the atoms in the carbon dioxide.

The relatively cool solvent with the captured carbon dioxide is directed, e.g., pumped, into and through a liquid-to-liquid heat pump (258) or heat exchanger. In an exemplary embodiment, the heat pump (258) heats the solvent to about 80° C. The heated solvent and the carbon dioxide are conveyed (260) to the second separation vessel (252).

In the second separation vessel (252), the heated solvent and carbon dioxide are sprayed through a nozzle (250) in a chamber of the second separation vessel (252). The carbon dioxide is released from the heated solvent due to the high temperature and is allowed to vent (264) out of the chamber of the second separation vessel (252) for further use, described below. The unsaturated solvent falls via gravity to the bottom (256) of the chamber of the second separation vessel (252) and is fed back to the heat pump (258). The cool solvent exiting the first separation vessel (246) and passing through the heat pump (258) cools the unsaturated solvent exiting the second separation vessel (252) and passing back through the heat pump (258). In an exemplary embodiment, the heat pump (258) cools the unsaturated solvent exiting the second separation vessel (252) to about 20° C. In an exemplary embodiment, the cooled and unsaturated solvent is conveyed (262) and reused by spraying the cooled solvent through the nozzle (248) back into the first separation vessel (246) for again capturing carbon dioxide of the dried emissions introduced via (245). In an exemplary embodiment, the process is continuous and carried out on a constant basis.

In an exemplary embodiment, the separation of carbon dioxide from a mixed gas stream via chemical capture (or absorption) efficiently integrates a two-chamber spray nozzle design for simultaneously capturing carbon dioxide from a mixed gas stream and subsequently releasing the captured carbon dioxide via thermal treatment. This embodiment efficiently integrates a liquid-to-liquid heat pump for optimizing the temperatures in the two-chamber carbon dioxide absorption system for the capture and release of carbon dioxide as required. It should be understood that the first separation vessel (246) and the second separation vessel (252) may be combined into a single vessel, and/or the heat pump (258) may be separate from or incorporated into either or both of the first and second separation vessels (246) and/or (252).

In step (108), water collected previously in step (104) is purified by boiling and/or distillation. In an exemplary embodiment, boiling and distillation are effective for conditioning, in more particularly purifying, the water for electrolysis and the subsequent production of hydrogen by electrolysis, discussed below.

In the system (200) of FIG. 2, the boiling and distillation of water (104) is completed in a distillation reactor or water purifier (280) that contains a heat exchanger for boiling water. In an exemplary embodiment, the water is received via conduit (282) from the condensate tank (234). The water purifier (280) may be embodied as a boiler and condenser for distilling the water received via conduit (282).

The boiling and condensation of water by the water purifier (280) are energy intensive steps. In an exemplary embodiment, waste heat is transferred via line (268) from the methanation reactor (266), discussed further below, to the water purifier (280) for boiling the water. The waste heat may be transferred via (268) in a molten salt, steam, or other fluid with a suitable heat capacity and mechanical characteristics. A dry cooler (212) uses an air-to-liquid heat exchanger to cool the heat transfer fluid (236), e.g., to 20° C., via ambient air entering through line (286). In an embodiment, a portion of the cooled heat transfer fluid is passed through (240) for condensation of the boiled water in the water purifier (280) using, for example, one or more coolant loops. The remaining portion of the cooled heat transfer fluid is passed through (240) to the condensate tank (234).

After the air (286) is heated by the heat transfer fluid (236), the heated air is discharged (288) back into the atmosphere (288) at, for example, about 90° C. The cooled heat transfer fluid (240) is fed into the water purifier (280), where the cooled heat transfer fluid (240) provides a heat sink to condense the boiled water to produce pure distilled water (278). The heated heat transfer fluid (236) is fed back into the dry cooler (212) for cooling. Notably, heat from the condensate tank (234) may likewise be discharged through line (237) using, e.g., the same heat transfer media or medium of (236), to the dry cooler (212), and the discharge (288).

In step (110) of FIG. 1, the purified water is subjected to electrolysis to generate hydrogen.

In an exemplary embodiment of the system (200), the purified water is discharged from the water purifier (280) via line (278) and fed to an electrolysis apparatus (276). In embodiments, the electrolysis apparatus (276) may be, for example, an alkaline, PEM, or radio-wave electrolysis system. The electrolysis apparatus (276) uses electricity to split purified water received via line (278) into hydrogen (274) and oxygen (297). However, the production of hydrogen via electrolysis can be throttled based on the supply of affordable electricity. In an exemplary embodiment, a system controller (290) connected in real-time via the Internet to real-time electricity markets and/or the performance of distributed electricity generation equipment decides based on project-specific economic parameters whether to open an electrical switch (292) that manages the supply of electricity (284) to the electrolysis apparatus (276) for carrying out the electrolysis. In an embodiment, the electrolysis apparatus (276) automatically segregates the hydrogen and oxygen that are produced. The hydrogen (274) is fed to the methanation reactor (266) and the oxygen (297) is mixed with the outside air inlet of the combustion appliance (224) to increase the overall combustion and process efficiency by increasing the oxygen to nitrogen ratio in the combustion chamber of the methanation reactor (266).

If needed or desired, an additional amount of water (or "make-up water") can be added to the electrolysis apparatus (276) to increase the hydrogen production for the subsequent methanation reaction. In an exemplary embodiment, the make-up water is delivered to the purifier (280) through line (282), if desired or needed, prior to electrolysis.

The next step (112) of FIG. 1 involves methanation. Carbon dioxide previously collected in separation step (106) is introduced, such as by injection, into a methanation reactor with hydrogen produced in electrolysis step (108) to produce combustible hydrocarbons, in particular at least methane.

As discussed further below, the hydrogen can be used in combination with carbon dioxide to produce combustible hydrocarbons such as methane. The production of methane from carbon dioxide requires hydrogen (274). Hydrogen production in an exemplary embodiment is completed in the electrolysis apparatus (276).

The system (200) of FIG. 2 is shown with a reactor, such as a catalytic methanation reactor (266). The carbon dioxide is introduced into the methanation reactor (266) via line (264) from the second separation vessel (252). The hydrogen is introduced into the methanation reactor (266) into the methanation reactor (266) via line (274) from the electrolysis apparatus (276). In an exemplary embodiment, the methanation reactor (266) is maintained at a temperature or temperatures in a range of 150° C. and 400° C., typically about 350° C. An appropriate catalyst, such as nickel, may be used to initiate a Sabatier reaction to produce the methane and water from the carbon dioxide and hydrogen.

The methane and water products are removed from the methanation reactor (266) via line (272) and are conveyed to a condensate tank (294). In an exemplary embodiment, the condensate tank (294) maintains a constant volume of water for immediately condensing the water out of the mixture of methane and water products (272). The methane (210) is subsequently transferred via line (298) to a compressor (208). In an embodiment, the compressor (208) pressurizes the methane to an ideal storage pressure of, for example, as much as 200 bar. The pressurized methane is transferred via line (202) to a storage tank (204) where the methane gas may be kept for a finite period or an indefinite time period, such as long as multiple years, if desired or required. The methane that is produced may be stored indefinitely and has an energy density more than 100 times that of a typical lithium-ion battery, which makes it a practical medium for serving as the basis for an economy that runs 100% on renewable energy.

In step (114), waste heat from methanation reactor (266) is recovered and reused. A Sabatier reactor may be used as the methanation reactor. In the exemplary system (200), the waste heat is conveyed via line (268) to the water purifier (280) to produce distilled water as precursor for electrolysis in the electrolysis apparatus (276). As mentioned above, in an exemplary embodiment the methanation reactor (266) operates at a minimum temperature of 150° C., and typically operates at a temperature of 350° C. Further, the synthesis of methane from hydrogen and carbon dioxide is an exothermic process that generates additional heat. In exemplary embodiments, the heat is removed using an appropriate heat sink in order to maintain a stable reactor temperature. For example, the boiler in the water purifier (280) can be used for this purpose, whereby the heat is transferred (268) via a molten salt, steam, or other fluid with a suitable heat capacity and mechanical characteristics from the methanation reactor to the boiler in the water purifier (280). The heat from the methanation reactor is utilized by the boiler to boil the water in the water purifier (280) as the initial and highly energy intensive step in water purification. The cooled heat transfer fluid (270) then returns to the methanation reactor (266) at a lower temperature, for example, approximately 150° C., and thus provides an essential heat sink for maintaining the thermal stability of the methanation reactor (266).

In step (116), the methane generated in step (112) is returned to step (102) for further combustion. In the system (200) of FIG. 2, when the methane stored in the storage tank (204) is needed for heat, electricity production, or mechanical energy, the methane is transferred via line (206) to the original combustion appliance (224) and/or another combustion appliance (not shown), where the methane is burned in the presence of air and the cycle returns to step (102) to output electricity (230).

Figure 3:
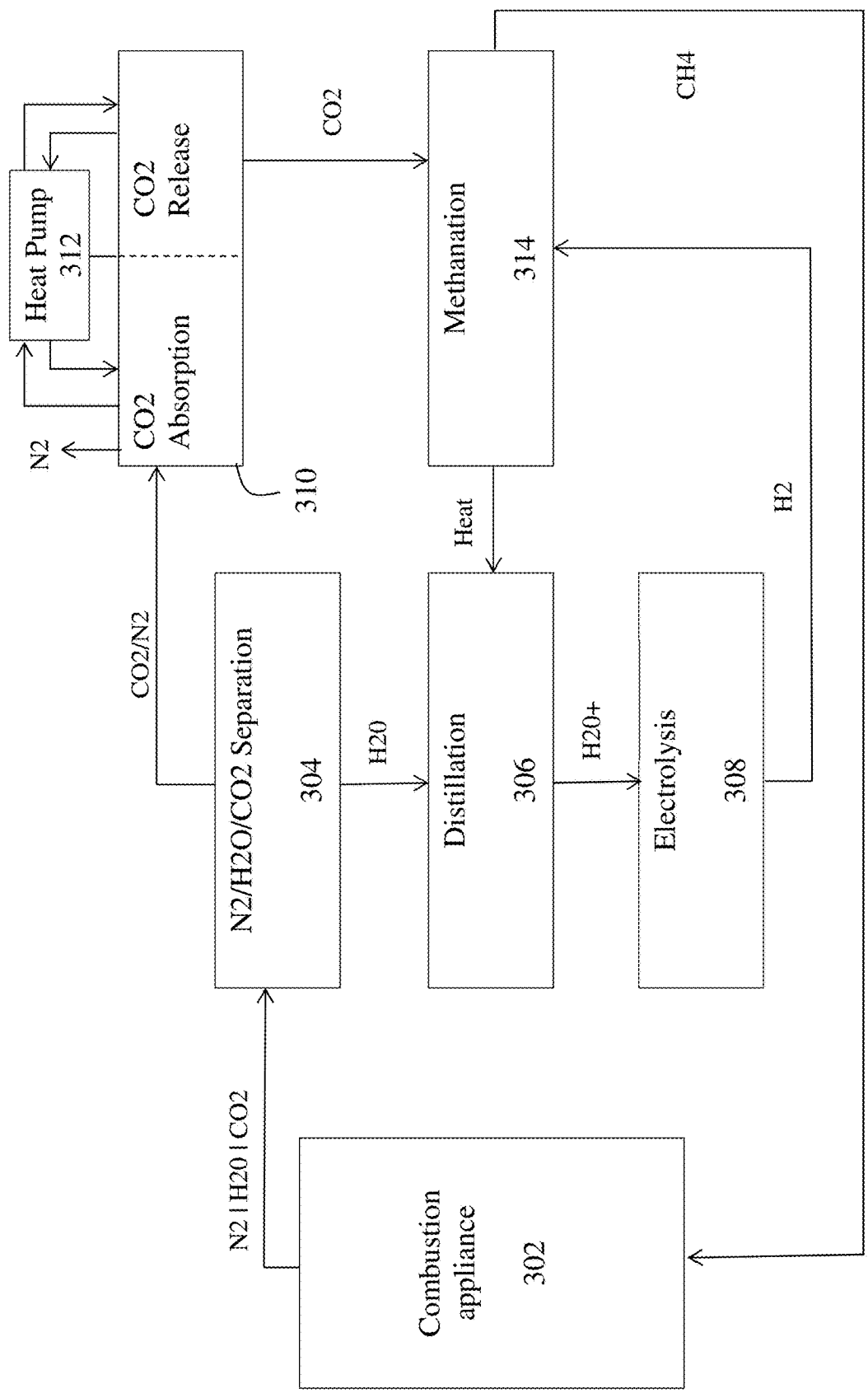
FIG. 3 is a simplified flow diagram showing interaction between different apparatus of the system of FIG. 2.

With reference to the flow diagram of FIG. 3, exemplary embodiments involve the integration of one or more of the following interactions or interrelations between steps and/or the system: (1) separation (304) of entrained water from combustion gases via condensation and/or desiccant drying provides a water source or water sources for distillation (306); (2) boiling and distillation of the water (306) using waste heat from methanation (314) to increase the overall efficiency of the process and system; (3) separation of carbon dioxide from an exhaust gas containing primarily nitrogen and carbon dioxide through the use of a liquid solvent in a continuous fashion (310) where a liquid-to-liquid heat pump (312) is utilized to cool the solvent for promoting the absorption of carbon dioxide, optionally to saturation, and to heat the saturated solvent to release the carbon dioxide from the solvent for further use of the heated solvent in heating the saturated solvent; and (4) methanation (314) of carbon dioxide from (310) with hydrogen from (308) to obtain methane gas according to the above equation (1); and (5) recycling of the methane gas from (314) to the combustion appliance (302).

Embodiments described above integrate elements utilize a Sabatier reactor and process in a scalable manner so that any source of carbon dioxide (e.g., combustion appliance (302)) may be retrofitted with our equipment in order to use intermittent renewable electricity to convert carbon dioxide emissions into methane. The result is an embodiment in which an existing fossil-fuel fired combustion appliance may be turned into a 100% carbon neutral system that maintains a closed loop on carbon:

Example

Combustion Appliance Operation and Output for Example

A basic model for understanding these steps may be modeled based on an application of this system to a combustion appliance embodied as a C65 Capstone Turbine (of Capstone Turbine Corporation), which is chosen by way of illustration and for exemplary purposes and should not be considered limiting of the scope of the described embodiments. The C65 Turbine produces 65 kW of continuous electricity and consumes natural gas (methane $CH_4$) at a rate of 888 MJ per hour. This fuel flow rate can be converted to other units as follows:

$$888 \text{ MJ/hr} \div 55 \text{ MJ/kg-CH}_4 = 16.15 \text{ kg-CH}_4/\text{hr} \quad (2)$$

$$16.15 \text{ kg-CH}_4/\text{hr} \div 16 \text{ g/mol(CH}_4) \times 10^3 \text{ g/kg} \div 3{,}600 \text{ sec/hr} = 0.28 \text{ mol-CH}_4/\text{sec} \quad (3)$$

Given that the carbon dioxide emissions quantity is directly related to the fuel consumed, the moles of carbon dioxide is related to the moles of methane consumed per the following basic stoichiometric equation:

$$CH_4 + 2(O_2 + 3.76N_2) \rightarrow CO_2 + 2H_2O + 7.52N_2 \quad (4)$$

Thus, the moles of methane burned are equivalent to the moles of carbon dioxide produced. For the example of the Capstone C65 turbine, there are 0.28 mol-$CO_2$/sec of carbon dioxide emissions produced during normal operation.

Nitrogen Separation for Example

The molar flow rate of 0.28 mol/sec $CO_2$ can be converted to a volumetric flow rate using the ideal gas law at exhaust conditions of 1 bar and 200° C. where 0.28 mol/sec equals 0.011 m³/sec. The volumetric flow rate of carbon dioxide is in turn related against the carbon dioxide removal capacity of the solvent, such as a sulfinol solvent, which is used for separating carbon dioxide from nitrogen in the exhaust gas stream. The carbon dioxide absorption capacity is 30-40 m³ $CO_2$/m³ sulfinol solvent. Carbon dioxide absorption capacities for different solvents are reported in Mahinder Ramdin, et al., *State-of-the-Art of CO2 Capture with Ionic Liquids*, Industrial & Engineering Chemistry Research (2012) 51 (24), 8149-8177 (DOI: 10.1021/ie3003705). Based on the absorption capacity of a sulfinol solvent and the flow a flow rate of carbon dioxide, it is possible to calculate the flow rate of a sulfinol solvent for capturing all of the carbon dioxide from the exhaust while venting the nitrogen into the atmosphere:

$$0.011 \text{ m}^3/\text{sec}(CH_4) \div 40 [\text{m}^3\text{-CO2/m}^3\text{-Sulfinol solvent}] \div 3{,}600 \text{ sec/Hr} = 0.99 \text{ m}^3/\text{sec (sulfinol)} = 4.36 \text{ Gallons/Minute(sulfinol)} \quad (5)$$

In an exemplary embodiment, the sulfinol solvent is heated and cooled on a constant basis in to order to captured carbon dioxide at, for example, 20° C. and then release the concentrated carbon dioxide at a higher temperature, for example, 80° C. In an exemplary embodiment, this is accomplished through the use of a liquid-to-liquid heat pump. An example of an adequately sized chiller/heat pump is the Trane Cold Generator™ Scroll Liquid Chillers, Models CGWR and CCAR, available from Ingersoll Rand. Those models require at least 6 kW of electricity to operate.

Electrolysis for Example

With a known flow rate of carbon dioxide, it is possible to calculate the quantity of hydrogen required to process all (100%) of the carbon dioxide into methane given the Sabatier reaction equation, below:

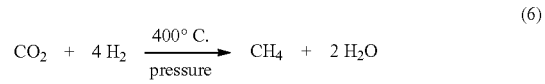

(6)

The requirement of 4 moles of hydrogen for every mole of carbon dioxide means that if the carbon dioxide flow rate is 0.28 mol/sec then the required hydrogen flow rate is 4× this amount or 1.12 mol/sec. Based on the flow rate of hydrogen it is possible to calculate the electricity required for electrolyzing water to produce hydrogen, which typically is the largest source of energy consumption in this process.

For the purposes of this example, the design basis for electrolysis performance is modeled based on the Hydrogenics HyLYZER® 600, which is chosen by way of illustration and for exemplary purposes and should not be considered limiting of the scope of the described embodiments. The HyLYZER® 600 can produce hydrogen at pressures up to 35 bar. Assuming a conservative hydrogen outlet pressure of only 2 bar, the volumetric flow rate of hydrogen can then be estimated with the ideal gas law at standard temperature to equal 46.80 m³/hr. Based on this flow rate of hydrogen and the power consumption requirements of the HyLYZER® 600 (3 MW/620 m³ hydrogen/hr), it is possible to calculate the net power consumption of electrolysis;

$$46.80 \text{-m}^3 \text{ hydrogen/hr} \div 620 \text{ m}^3 \text{ hydrogen/gr} \times 3 \text{ MW} = 226.45 \text{ kW} \quad (7)$$

Thus for the C65 Capstone Turbine, a calculated 226.45 kW of electricity are required to produce the hydrogen flow rate to continuously convert 100% of the carbon dioxide emissions into methane.

Sabatier Reaction for Example

Converting carbon dioxide and hydrogen into methane is typically conducted at about 350° C. over a suitable (e.g., nickel) catalyst. A reasonable efficiency, in terms of moles of methane produced per moles of carbon dioxide processed, is about 80%. The calculation of the methane produced from the process with the C65 Capstone Turbine is thus:

$$0.28 \text{ mol-CO}_2/\text{sec} \times 80\% \text{ Sabatier efficiency} = 0.22 \text{ mol-CH}_4/\text{sec} \quad (8)$$

$$0.22 \text{ mol-CH}_4/\text{sec} \times 16 \text{ g-CH}_4/\text{mol} \div 10^3 \text{ g/kg} \times 55 \text{ MJ/kg-CH}_4 = 197.33 \text{ kW} \quad (9)$$

Energy Calculations for Example

Given an energy consumption of 6 kW for the nitrogen separation, 226.45 kW for the electrolysis, and an energy output of 197.33 kW for methanation, the net energy budget of the example process are calculated to be 35.12 kW of net power consumption. In terms of power consumption per weight of CO2:

$$35.12 \text{ kW} \div \{0.28 \text{ mol-CO}_2/\text{sec} \times 44 \text{ g-CO}_2/\text{mol} \times 3{,}600 \text{ sec/Hr} \div 10^6 \text{ g/tonne}\} = 791 \text{ kWh/tonne-CO2} \quad (10)$$

Based on the above calculations, the energy requirement for carbon dioxide abatement from the C65 Capstone Turbine is calculated to be 791 kWh per tonne of carbon dioxide removed. While the cost of carbon dioxide emission credits and electricity varies radically based on location, this parameter is economically robust for most applications. Balancing the electricity grid is already a major issue throughout the world where utility operators strive to ensure that the supply and demand of electricity are always matched. Current causes for this challenge are driven by weather-driven spikes in electricity demand and/or inflexible sources of electricity supply such as nuclear and large coal power plants that are difficult to modulate. The increasing utilization of renewable electricity is aggravating the challenge of balancing the grid to an extreme degree. B. Aust et al., *Negative market prices on power exchanges: evidence and policy implications from Germany*, Electricity Journal, Vol. 33, Issue 3 (2020), 106716, ISSN 1040-6190. As a result, electricity prices are increasingly negative for significant portions of time in order to remove excess electricity from the power grid, where consumers are paid to use electricity. This approach to carbon dioxide abatement makes it possible to directly profit from the conversion of carbon dioxide to methane because operators may be paid to use electricity to convert carbon dioxide into methane which in turn is a valuable commodity. In markets where negative electricity pricing is not available, the price of carbon is increasingly large enough to ensure profitable operation. For example, in New York City, USA, the price of carbon dioxide based on the recently passed Climate Mobilization act is \$268/tonne-$CO_2$ and thus even at electricity prices as high as \$0.20/kWh there is still a net profit from this process of about \$100 per tonne-$CO_2$ abated.

The energy generated from the methane produced according to this example process can be calculated as follows:

$$\frac{0.22 \text{ mol CH4/sec} \times 16 \text{ g}\frac{CH4}{mol} \times 55 \frac{MJ}{kg} CH4 \times 1 \frac{kg}{1,000} g}{0.28 \text{ mol CO2/sec} \times 44 \text{ g}\frac{CO2}{mol} \times \frac{tonne}{1,000,000} g} = \quad (11)$$

$$15,714.29 \text{ MJ CH}_4/O_2 = 410.29 \text{ m}^3 \text{ CH}_4/\text{tonne CO}_2.$$

The electricity requirements for producing this methane according to this example can be similarly calculated:

$$\frac{6 \text{ kW}(N2 \text{ seperation}) + 226.45 \text{ kW(electrolysis)}}{\left(0.28 \text{ mol}\frac{CO2}{sec}\right)\left(44 \text{ g}\frac{CO2}{mol}\right)\left(3,600\frac{sec}{hr}\right)\left(\frac{tonne}{1,000,000}g\right)} = \quad (12)$$

$$5,235.40 \text{ kW/tonne CO}_2$$

The water requirements based on electrolysis for the example process are calculated as follows:

$$\frac{\left(1.12\frac{mol}{sec}H2O\right)\left(18\frac{g}{mol}H2O\right)\left(\frac{kg}{1,000 g}\right)(3,600 \text{ sec/hr})\left(\frac{m3}{1000 kg}\right)}{(0.28 \text{ mol/sec CO2})\left(\frac{44 g}{mol}CO2\right)\left(\frac{tone}{1,000,000 g}\right)} = \quad (13)$$

$$5,925 \text{ m}^3 \text{ H}_2\text{O/ tonne (CO)}_2$$

Given the integration of a combined cycle power plant with an efficiency of 60% the electricity produced from the methane generated is as follows:

$$(15,714.29 \text{ MJ CH}_4/\text{tonne CO}_2) \times 0.60 = 9,428.57$$
$$\text{MJ-CH}_4/\text{tonne-CO}_2 = 2,619 \text{ kW/tonne CO}_2 \quad (14)$$

Embodiments disclosed herein are directed to systems and method configured to achieve, in particularly exemplary embodiments, at least one of the following objects and advantages. First, combustion emissions, such as from a hydrocarbon combustion appliance or system, are isolated and reused. In an exemplary embodiment, carbon dioxide and hydrogen isolated from the combustion emissions are converted into hydrocarbons, such as methane via methanation. Second, waste heat generated by methanation can be utilized in other parts of the process and system, such as in the production of distilled water that can serve as a precursor for the generation of the hydrogen via electrolysis. Third, water from the combustion emissions can be separated, boiled, distilled, and electrolyzed in an efficient manner for the purpose of generating hydrogen for the methanation reaction. Fourth, in an exemplary embodiment a device such as a liquid-to-liquid heat pump is utilized to maintain carbon dioxide solvent such as a sulfinol solvent at an optimum temperature for capturing and releasing carbon dioxide from a mixed gas stream. Fifth, the combustion emissions exhaust stream can be recycled back into a power plant or other system from which is was recovered for further use and/or can be put to other uses.

It should be understood that the process is scalable, including, for example and not by limitation, from a 5 kW residential backup generator to a 500 MW power plant.

In a particularly advantageous embodiment, the method and system may be integrated with one or more natural energy sources, such as photovoltaic solar cells, to operate equipment of system and carry out steps of the method. For example, photovoltaic energy may be used to power the electrolysis, nitrogen separation liquid-to-liquid chiller/heat pump, the dry cooler, the compressor for methane compression, pumps, fans, control systems, peripheral loads, or any combination thereof. In an exemplary embodiment, the method and system are practiced without the use of fossil fuels.

Embodiments disclosed herein efficiently integrate thermal separation of water and chemical capture/absorption of carbon dioxide to separate carbon dioxide from other constituents in exhaust including but not limited to water and nitrogen.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any claim unless recited in the claim.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

The various components and features of the above-described exemplary embodiments may be substituted into one another in any combination. It is within the scope of the invention to make modifications necessary or desirable to incorporate one or more components and features of any one embodiment into any other embodiment. One skilled in the art, using the disclosures provided herein, will appreciate that various steps of the methods can be omitted, rearranged, combined, supplemented with additional steps, and/or adapted in various ways.

The foregoing description of the exemplary embodiments and exemplary methods has been provided for the purpose of explaining principles of the invention and its practical application, thereby enabling others skilled in the art to understand the invention for various embodiments and with various modifications as are suited to the particular use contemplated. The description is not necessarily intended to be exhaustive or to limit the invention to the precise embodiments disclosed.

The flowchart and block diagrams in the Figures illustrate the architecture, functionality, and operation of possible implementations of systems and methods according to various embodiments of the present embodiments. In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved.

It will be appreciated that, although specific embodiments have been described herein for purposes of illustration, various modifications may be made without departing from the spirit and scope of the embodiments. Accordingly, the scope of protection of the embodiments is limited only by the following claims and their equivalents.

What is claimed is:

1. A method comprising:
   receiving a hydrocarbon combustion exhaust stream comprising water and carbon dioxide;
   removing at least a portion of the water to at least partially dry the hydrocarbon combustion exhaust stream;
   separating the carbon dioxide from the at least partially dried hydrocarbon combustion exhaust stream, the separating comprising capturing the carbon dioxide in a solvent, heating the solvent and the captured carbon dioxide, and removing the carbon dioxide from the heated solvent;
   subjecting the removed water to electrolysis to generate hydrogen; and
   reacting the generated hydrogen and the separated carbon dioxide to generate one or more hydrocarbons, including at least methane.

2. The method of claim 1, wherein the hydrocarbon combustion exhaust stream comprises steam, and wherein the removing comprises condensing the steam of the hydrocarbon combustion exhaust stream.

3. The method of claim 2, wherein the condensing comprises injecting the hydrocarbon combustion exhaust stream into liquid water.

4. The method of claim 2, wherein the condensing comprises passing the hydrocarbon combustion exhaust stream through a heat exchanger.

5. The method of claim 2, wherein the removing at least a portion of the water further comprises introducing the hydrocarbon combustion exhaust stream to a desiccant dehumidifier.

6. The method of claim 5, further comprising:
   boiling and distilling the removed water prior to the electrolysis; and
   transferring heat from the boiling to the desiccant dehumidifier to dry a desiccant thereof.

7. The method of claim 1, wherein the solvent comprises a sulfinol solvent.

8. The method of claim 1, wherein:
   the capturing of the carbon dioxide in the solvent comprises spraying the solvent on the at least partially dried hydrocarbon combustion exhaust stream to capture the carbon dioxide in the solvent in a first chamber; and
   the removing the captured carbon dioxide from the solvent comprises heating the solvent with the carbon dioxide captured therein to release the carbon dioxide from the heated solvent in a second chamber.

9. The method of claim 8, further comprising:
   discharging the solvent with the carbon dioxide captured therein from the first chamber and passing the discharged solvent and carbon dioxide from the first chamber through a heat pump to heat the solvent; and
   discharging the heated solvent from the second chamber and passing the discharged heated solvent from the second chamber through the heat pump to heat the solvent and carbon dioxide discharged from the first chamber.

10. The method of claim 1, further comprising boiling and distilling the removed water prior to the electrolysis.

11. The method of claim 10, further comprising transferring heat generated by the reacting of the generated hydrogen and the separated carbon dioxide to the removed water for the boiling.

12. The method of claim 1, wherein the reacting comprises feeding the generated hydrogen and the separated carbon dioxide to a methanation reactor for catalytic reaction to generate the methane.

13. The method of claim 1, further comprising generating oxygen by the electrolysis, and transferring the oxygen generated by the electrolysis to a combustion appliance.

14. The method of claim 1, further comprising compressing the methane and storing the compressed methane.

15. A method comprising:
   receiving a hydrocarbon combustion exhaust stream comprising water and carbon dioxide;
   removing at least a portion of the water to at least partially dry the hydrocarbon combustion exhaust stream;
   capturing the carbon dioxide in a solvent in a first chamber;
   using a heat pump, heating the solvent with the captured carbon dioxide;
   separating the carbon dioxide from the heated solvent in a second chamber that is different than the first chamber;
   subjecting the removed water to electrolysis to generate hydrogen; and
   reacting the generated hydrogen and the separated carbon dioxide to generate one or more hydrocarbons, including at least methane.

16. The method of claim 15, wherein the capturing of the carbon dioxide in the solvent comprises spraying the solvent on the at least partially dried hydrocarbon combustion exhaust stream in the first chamber.

17. The method of claim 15, wherein the separating of the carbon dioxide from the heated solvent in the second chamber comprises:
   spraying the heated solvent in the second chamber to release the carbon dioxide; and
   venting the released carbon dioxide from the second chamber.

18. The method of claim 15, wherein the hydrocarbon combustion exhaust stream comprises steam, and wherein the removing at least a portion of the water comprises:
  condensing the steam of the hydrocarbon combustion exhaust stream; and
  introducing the hydrocarbon combustion exhaust stream to a desiccant dehumidifier.

19. The method of claim 18, further comprising:
  boiling and distilling the removed water prior to the electrolysis; and
  transferring heat from the boiling to the desiccant dehumidifier to dry a desiccant thereof.

20. A method comprising:
  receiving a hydrocarbon combustion exhaust stream comprising water and carbon dioxide;
  removing at least a portion of the water to at least partially dry the hydrocarbon combustion exhaust stream;
  capturing the carbon dioxide in a solvent in a first chamber;
  using a heat pump, receiving the solvent with the carbon dioxide captured therein from the first chamber;
  separating the carbon dioxide from the heated solvent in a second chamber that is different than the first chamber;
  using the heat pump, receiving the heated solvent from the second chamber and heating the solvent received from the first chamber with the heated solvent while cooling the heated solvent received from the second chamber;
  subjecting the removed water to electrolysis to generate hydrogen; and
  reacting the generated hydrogen and the separated carbon dioxide to generate one or more hydrocarbons, including at least methane.

21. The method of claim 20, wherein the capturing of the carbon dioxide in the solvent comprises spraying the solvent on the at least partially dried hydrocarbon combustion exhaust stream in the first chamber.

22. The method of claim 20, wherein the separating of the carbon dioxide from the heated solvent in the second chamber comprises:
  spraying the heated solvent in the second chamber to release the carbon dioxide; and
  venting the released carbon dioxide from the second chamber.

23. The method of claim 20, wherein the hydrocarbon combustion exhaust stream comprises steam, and wherein the removing at least a portion of the water comprises:
  condensing the steam of the hydrocarbon combustion exhaust stream; and
  introducing the hydrocarbon combustion exhaust stream to a desiccant dehumidifier.

24. The method of claim 23, further comprising:
  boiling and distilling the removed water prior to the electrolysis; and
  transferring heat from the boiling to the desiccant dehumidifier to dry a desiccant thereof.

25. The method of claim 1, wherein the received hydrocarbon combustion exhaust stream further comprises nitrogen, and wherein the separating of the carbon dioxide from the at least partially dried hydrocarbon combustion exhaust stream further comprises separating the carbon dioxide from the nitrogen of the at least partially dried hydrocarbon combustion exhaust stream.

26. The method of claim 15, further comprising:
  boiling and distilling the removed water prior to the electrolysis; and
  transferring heat generated by the reacting of the generated hydrogen and the separated carbon dioxide to the removed water for the boiling.

27. The method of claim 15, wherein the received hydrocarbon combustion exhaust stream further comprises nitrogen, and wherein the capturing the carbon dioxide in the solvent in the first chamber further comprises separating the carbon dioxide from the nitrogen of the at least partially dried hydrocarbon combustion exhaust stream.

28. The method of claim 20, further comprising:
  boiling and distilling the removed water prior to the electrolysis; and
  transferring heat generated by the reacting of the generated hydrogen and the separated carbon dioxide to the removed water for the boiling.

29. The method of claim 20, wherein the received hydrocarbon combustion exhaust stream further comprises nitrogen, and wherein the capturing the carbon dioxide in the solvent in the first chamber further comprises separating the carbon dioxide from the nitrogen of the at least partially dried hydrocarbon combustion exhaust stream.

* * * * *